United States Patent [19]
Johnson

[11] Patent Number: 5,522,844
[45] Date of Patent: Jun. 4, 1996

[54] SUTURE ANCHOR, SUTURE ANCHOR INSTALLATION DEVICE AND METHOD FOR ATTACHING A SUTURE TO A BONE

[76] Inventor: Lanny L. Johnson, 4528 Hagadorn, East Lansing, Mich. 48823

[21] Appl. No.: 79,730

[22] Filed: Jun. 22, 1993

[51] Int. Cl.⁶ .................................................. A61B 17/04
[52] U.S. Cl. ......................... 606/232; 606/104; 606/75; 411/447; 411/495
[58] Field of Search ...................... 606/232, 139, 606/219, 72, 75, 104, 220; 411/447, 487, 495, 498; D24/145; 24/297, 662

[56] References Cited

U.S. PATENT DOCUMENTS

| | | | |
|---|---|---|---|
| D. 281,814 | 12/1985 | Pratt et al. | D24/27 |
| D. 284,509 | 7/1986 | Johnson | D24/29 |
| D. 286,442 | 10/1986 | Korthoff et al. | D24/27 |
| D. 320,081 | 9/1991 | Johnson | D24/145 |
| 4,579,473 | 4/1986 | Brugger | 24/297 |
| 4,635,637 | 1/1987 | Schreiber | 128/337 |
| 4,898,156 | 2/1990 | Gatturna et al. | 606/72 |
| 4,932,960 | 6/1990 | Green et al. | 606/220 |
| 4,946,468 | 8/1990 | Li | 606/232 |
| 5,013,316 | 5/1991 | Goble et al. | 606/72 |
| 5,046,513 | 9/1991 | Gatturna et al. | 128/898 |
| 5,065,490 | 11/1991 | Wivagg et al. | 24/297 |
| 5,141,520 | 8/1992 | Goble et al. | 606/232 |
| 5,203,784 | 4/1993 | Ross et al. | 606/104 |

FOREIGN PATENT DOCUMENTS

| | | | |
|---|---|---|---|
| 2334869 | 7/1977 | France | 411/495 |

*Primary Examiner*—Gary Jackson
*Attorney, Agent, or Firm*—Cushman Darby & Cushman

[57] ABSTRACT

A suture anchor to secure a suture within a bore in a bone is disclosed, together with a suture anchor installation tool and method for deploying the suture anchor using the installation tool. The anchor includes a cylindrical body portion integrally associated with a generally conical-shaped end portion. At least one slot extends from the apex of the conical-shaped end portion into the cylindrical body portion forming at least two deformable tines. The tines flex toward one another as the anchor is inserted into the bore and are sufficiently resilient so as seek to return to an undeformed position once in the bone. The tines include outer edges disposed at the base of the conical-shaped end portions for preventing the suture anchor from being pulled out of the bore. The suture anchor installation tool includes an insertion member having an elongated body with a hollow interior sized so as to accommodate the suture anchor therein. The elongated body includes a suture loading assembly enabling a suture to be threaded through the slot while the anchor is fully retained in the elongated body.

19 Claims, 5 Drawing Sheets

SUTURE ANCHOR, SUTURE ANCHOR INSTALLATION DEVICE AND METHOD FOR ATTACHING A SUTURE TO A BONE

BACKGROUND OF THE INVENTION

1. Field of the Invention

The present invention relates to an anchoring device for affixing a surgical suture to a bone and an installation tool for deploying same.

2. Description of the Related Art

Various surgical procedures require soft tissue, such as ligaments, tendons, muscles and the like, to be attached to bone. Such surgical procedures include, for example, repairing knee and ankle ligaments, rotator cuff tears, and glenohumeral instability. In certain situations, it is desirable to anchor a suture to a bone and then use the suture to attach the tissue to the bone.

Various devices are known for affixing a surgical suture to a bone. One such device consists of a staple-like structure having at least two leg portions and a body disposed between the legs. This staple-like device is attached to bone by driving the legs into the bone so that a suture can be secured between the bone and the body of the staple. This procedure, however, is often difficult to perform in areas where access to the bone is limited. As a result, it is frequently necessary to place the staple at a less than desirable location. Furthermore, a plurality of bores must be made in the bone in order to secure the suture thereto, which has obvious disadvantages.

Another suture anchor, taught by U.S. Pat. No. 5,141,520, consists a cylindrical body and a solid conical-shaped harpoon-type head attached to the body. A suture is attached to this harpoon-type anchor by securing one of its ends within the anchor body with the other end extending from the rear thereof. The solid conical-shaped head enables the anchor to be driven into bone without first drilling a bore. Once in the bone, a flexible skirt around the base of the conical-shaped head acts as a barb to hold the anchor in place.

It can be difficult to achieve a proper level of flexibility in the skirt to enable the skirt to spread away from the anchor widely enough to engage a relatively large portion of the interior surface of the bone and yet be flexible enough to enable the anchor to be driven into the bone without excessive resistance. Furthermore, because only one end of the suture extends from the bone, two such harpoon suture anchor devices must be driven into the patient's bone if two suture ends are needed to attach the tissue to the bone. This has obvious disadvantages. Also, it is impossible to substitute one suture for another in a given anchor because the suture is fixedly secured within the body of the anchor. To use different sutures during a given surgical procedure, the surgeon must have a number of pre-loaded suture anchors at his disposal. Furthermore, there is the possibility for the end of the suture to detach from body, due to the difficulties inherent in affixing one end of a suture into a solid object.

The harpoon-type suture anchor is driven into the bone using a hollow driving rod. The anchor is loaded into one end of the rod such that the conical head projects from the rod, with the rear of the anchor, including the suture, disposed within the rod. The anchor is driven into the bone by a hammer force transmitted through the rod. Depending on the strength of the bone, a large amount of force may be required to insert the anchor. Thus, the surgeon must be highly skilled to ensure that the driving force is properly applied to the anchor and that the anchor is not driven too far into the bone. Moreover, the greater the force required to insert the suture anchor, the greater the probability that the rod and/or suture anchor will be damaged. Also, the trauma to the patient's bone and surrounding tissue increases. Because a portion of the anchor is disposed within the driving rod, there is the possibility that the anchor will not properly pull out of the rod once in the bone.

In other types of suture anchor devices the anchor is not driven directly into the bone but instead is placed within a bore formed in the bone. One such device, taught by U.S. Pat. Nos. 4,898,156 and 5,046,513, consists of a metal cylindrical body having at least one flexible tail or barb extending from a rear end thereof. The body and barb are inserted into a bore prepared in the bone. The flexible barb is straightened as the anchor is inserted into the bore and returns to its original curved position to engage the side wall of the bore, once fully inserted, thus preventing the anchor from being pulled out of the bore. In this device, however, the barb may unwantedly penetrate the side wall of the bore due to the fact that the barb has a relatively narrow portion that engages the side wall. Additionally, this type of anchor may be rendered ineffective should the barb: be too flexible; not properly engage the side wall; break; or become detached from the body of the anchor. It is not possible to insert this anchor into a bore so that the rear end of the anchor is flush with the bone surface, because the barb must be fully seated within the bore.

In the type of suture anchor just described, only one end of the suture is attached to the anchor body. Specifically, a knot tied in the suture holds the suture within the anchor body. The free end of the suture extends from the body and out of the bore. This method of attaching the suture to the anchor suffers the same disadvantages discussed above with respect to the harpoon-type suture anchor device wherein only one end of the suture is available to attach tissue to the bone. Also, there is always the possibility that the knot may become undone. Furthermore, if the suture is attached such that it does not extend from the anchor along its longitudinal axis, or if the anchor is not held within the bore such that its longitudinal axis is parallel to the centerline of the bore, tension on the suture will impart a torque on the anchor due the asymmetrical load applied to the anchor. This torque can cause the anchor to twist within the bore resulting in the barb undesirably penetrating the side wall.

One installation tool for deploying the just-described anchor into the bore consists of a tubular body member into which the anchor is loaded tail first so that the barb extends straight from the body into the hollow portion of the installation tool. A plunger slidably disposed within the tubular body forces the anchor into the bore. Because the barb projects beyond the rear of the anchor, the plunger must engage the barb during the insertion procedure. This has a disadvantage in that the flexibility of the barb may not provide a solid surface for the plunger to act upon. Also, there is a possibility that the plunger force acting on the barb may damage the barb or its attachment to the anchor body.

In this type of insertion device, the end of the tubular body within which the anchor is disposed must be placed in the bore so that the anchor can be expelled from the insertion device fully within the bore. Therefore, it is necessary to dimension the bore wide enough to receive the anchor and the surrounding end portion of the insertion device. Consequently, a bore wider than just the anchor is required. The wider bore can allow the anchor to twist undesirably therein, especially when an asymmetrical load is applied on the anchor. Furthermore, skill is required to ensure that the insertion device is not placed too far into the bore and to position the anchor within another bore at the same depth on repeated occasions.

To attach the suture to the anchor while using the installation tool just described, the anchor must be pushed out of the insertion device far enough for the person loading the suture to access the anchor body. Thereafter, the suture must be tied in a knot and loaded into the anchor. This is a relatively complicated and delicate procedure, making changes in the type or size of suture difficult and time consuming.

A second known embodiment for the just described installation tool consists of the above described tubular body and plunger and also incudes a hollow loading member. Instead of loading the anchor into the tubular body, the anchor first is loaded tail first into an end of the loading member so that the body of the anchor around the barb abuts the end of the loading member. The loading member, with the anchor therein, is then inserted into an end of the tubular member opposite that just discussed above. Actuating the loading member positions the anchor outside the insertion device for attaching the suture. The plunger is used to deploy the anchor from the loading member and tubular member as discussed above. While this type of installation device makes it easier to access the anchor for loading the suture, it has three elements, is relatively complicated, and the procedure for using it must be performed carefully so as not to damage the suture anchor. Also, a significant amount of time is required to align the ends of the anchor with the ends of the installation members and to align the ends of the installation tools with one another. As a result, quickly loading a series of anchors in one installation tool is difficult.

As with the previous installation tool, the end of the tubular member must be placed within the bore necessitating the use of bore wider than the anchor. Also, skill is required to ensure that the tubular member is properly placed into the bore and to consistently position the anchor within the bore at the same depth.

A further type of anchor is taught by U.S. Pat. No. 4,946,468 and is structurally similar to the barb-type suture anchor discussed above. In this anchor, the suture is wrapped around a pin in the anchor body so that both ends of the suture extend from the bore. However, each suture end extends from the bore at substantially the same location, which can result in unwanted tangling and knotting of the suture. This barb-type anchor also suffers from many of the disadvantages discussed above with respect to the first-described barb-type anchor. For example, the rear of anchor can not be inserted flush with the bone surface, the barb is susceptible to breaking or malfunctioning, and the anchor may twist within the bore.

The installation tool for inserting this further version of a barb-type anchor includes a handle with a cannula attached thereto. The anchor is fitted into an end of the cannula such that a portion of the anchor remains outside the cannula. A slot in the canula receives the barb so that the barb remains in its unflexed, curved position. A suture is attached to the portion of the anchor remaining outside the cannula. Loading the suture can still be difficult and time consuming, because the suture must be threaded into the anchor body, wrapped around the pin, and then threaded back out of the body.

The anchor is inserted into a bore by pushing the cannula with the loaded anchor into the bore through the actuation of the handle. The anchor is pulled out of the cannula by the engagement of the barb with a side wall of the bore. Using the barb to dislodge the anchor from the insertion device can result, however, in unwanted force on the barb and on the side wall of the bore, especially if the anchor fails to slide easily out of the cannula. On the other hand, if the anchor slides out of the cannula too easily, it can be difficult to keep the anchor in the cannula, especially when loading the suture. As with the previous insertion devices there is no means to ensure that the anchor is inserted to the same depth in repeated procedures. Instead, the surgeon must judge when the anchor is inserted far enough into the bore.

SUMMARY OF THE INVENTION

It is an object of the present invention to provide a suture anchor and a suture anchor insertion device which overcomes the problems associated with the prior art as discussed above. In accordance with the principles of the present invention, this objective is achieved by providing a suture anchor adapted to secure a length of surgical suture within a bore formed in a bone. The suture anchor includes a generally cylindrical body portion and a generally conical portion coaxially attached at its base to the body portion. The anchor includes at least one slot extending from the apex of the conical portion into the body portion for receiving a suture therein so as to define at least a first and second flexible tine on opposite sides of the slot.

According to the preferred embodiment of the present invention, the foregoing suture anchor is used in conjunction with a suture anchor installation tool which includes an insertion member. The insertion member includes an elongated body with a hollow interior sized to receive the suture anchor therein. The elongated body also includes a suture loading assembly enabling a suture to be loaded within the slot in the anchor by threading the suture straight through the slot while the anchor is fully retained within the interior of the elongated body. In an additional embodiment of the present invention, the elongated body member includes an aligning means cooperating with the slot for positioning the anchor within the elongated body such that the slot is aligned with the suture loading means.

It is another object of the present invention to provide a method of anchoring an intermediate portion of a suture within a bore formed in a bone using the suture anchor installation tool to insert the suture anchor of the present invention including a suture loaded therein into the bone.

It is a further object of the present invention to provide a suture anchor and suture anchor insertion device which are simple in construction, economical to manufacture, and effective in operation.

These and other objects of the present invention will become more apparent during the course of the following detailed description and appended claims.

The invention may best be understood with reference to the accompanying drawings wherein illustrative embodiments are shown.

DETAILED DESCRIPTION OF THE PREFERRED EXEMPLARY EMBODIMENT

Figure 1:
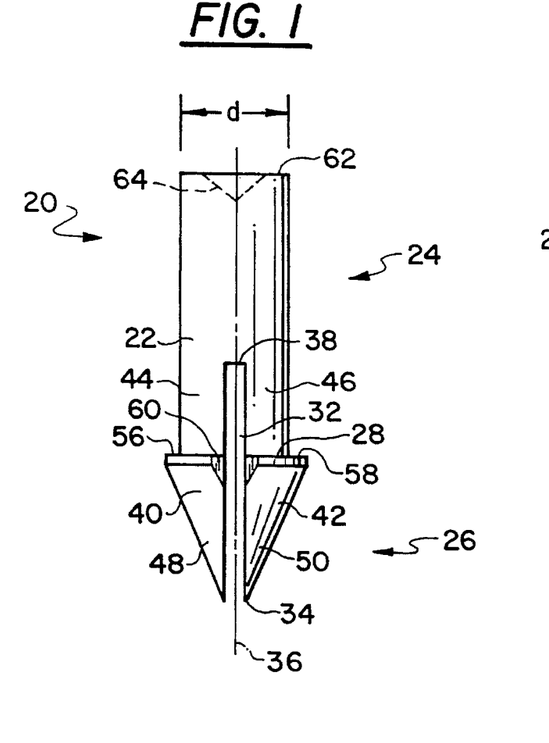
FIG. 1 is a side elevational view of the suture anchor according to the present invention.
Figure 2:
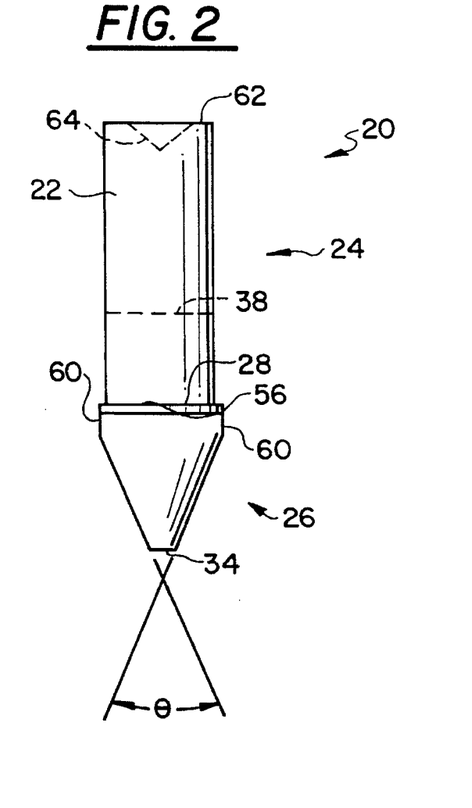
FIG. 2 is a front elevational view of the suture anchor shown in FIG. 1.
Figure 3:
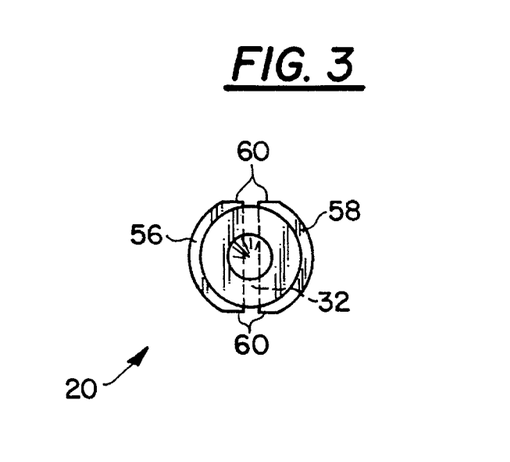
FIG. 3 is a plan view of the suture anchor shown in FIG. 1.

Referring to the drawings, FIGS. 1–3 illustrate a suture anchor device, generally indicated at 20, according to the present invention. More particularly, the anchor 20 comprises a body 22 having a generally cylindrical body portion 24 integrally associated with a coaxially aligned conical portion 26 of substantially conical shape. The base of the portion 26 is of greater diameter than that of portion 24 thereby defining a shoulder 28 where portions 24 and 26 meet.

The body 22 is provided with a slot 32 extending from the apex 34 of the portion 26 along the common longitudinal axis 36 of portions 24 and 26. The slot 32 extends beyond shoulder 28 to a location 38 within portion 24 whereby first and second flexible tines 40 and 42 are defined at one end of the anchor 20. Slot 32 is dimensioned in width to receive an intermediate portion of a length of surgical suture, as will be described hereinafter with respect to FIG. 5.

The tines 40 and 42 consist of semi-cylindrical stem portions 44 and 46, and tapered portions 48 and 50. The tapered portions 48 and 50 are segments of the conical-shaped portion 26. Because the base of portion 26 has a diameter greater than that of the body 22, at the intersection of the tapered portions 48 and 50 with the stem portions 44 and 46, outer edge portions 56 and 58 are exposed (FIG. 3). The tapered portions 48 and 50 are tapered such that an angle Θ of approximately 47° is formed (FIG. 2).

Outer edge portions 56 and 58 have flattened ends 60, which provide additional strength to the tapered portions 48 and 50. Also, the end 62 of the body 22 includes a depression 64 therein, the purpose of which is discussed hereinafter. It is to be understood that the body 22 and the first and second deformable tines 40 and 42 preferably are formed as a molded piece of a plastic material suitable for implantation within a bone in the body.

Figures 4A, 4B:
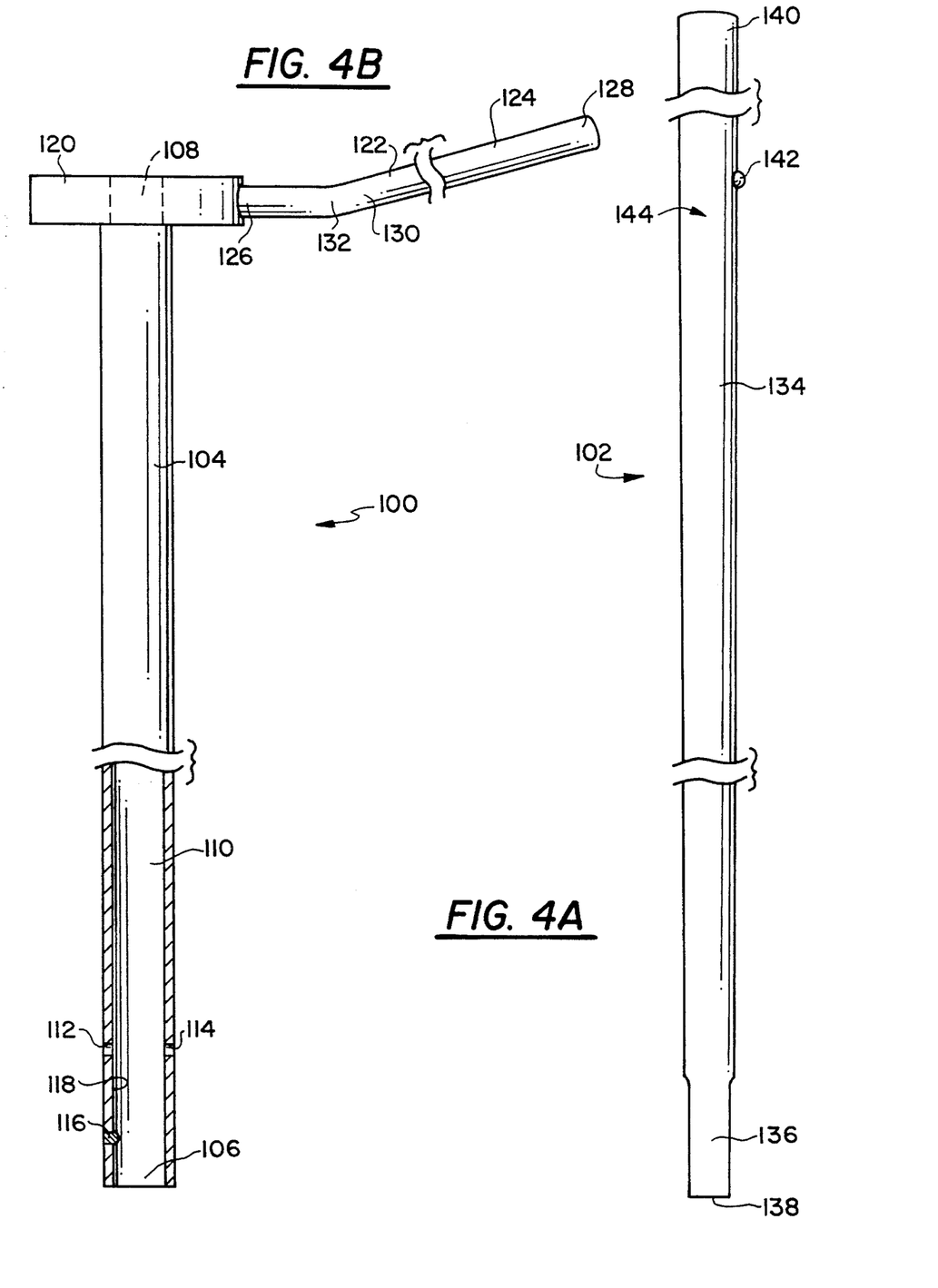
FIGS. 4A and 4B are front elevational views, partially in section, illustrating separately the two members which comprise a suture anchor installation tool suitable for inserting the suture anchor of FIG. 1 into bone.

Referring now to FIGS. 4A and 4B, there is shown therein the two members which comprise a suture anchor installation tool suitable for deploying the suture anchor shown in FIGS. 1–3 into a bone. The suture anchor installation tool includes a cylindrical suture anchor insertion member, generally indicated at 100, and a plunger, generally indicated at 102. The insertion member 100 includes an elongated body 104 having a first end 106, a second end 108, and a hollow interior portion 110 dimensioned so as to accommodate therein the anchor 20 of FIGS. 1–3. The elongated body 104 includes a suture loading means disposed proximate to the end 106. The loading means consists of a first and second hole 112 and 114 through the elongated body 104 and aligned on opposite sides thereof.

The elongated body 104 also includes a suture anchor aligning means for positioning the suture anchor (not shown) within the interior portion 110 of the insertion member 100. The aligning means consists of a protruding appendage 116 disposed on an interior surface 118 of the body member 110 between the end 106 and holes 112 and 114. The elongated body 104 also includes, a flange 120 disposed at end 108. A handle 122 is attached to the flange 120. The handle 122 includes a rod member 124 having ends 126 and 128, and a midsection 130 disposed therebetween. End 126 is attached to the flange 120, and the midsection 130 has a bend 132 therein.

The plunger 102 is dimensioned so as to be slidably receivable within the interior portion 110 of the elongated body 104. It consists of a solid body portion 134, a tapered end 136 having an end surface 138, and an opposite end portion 140. The plunger 102 includes a suture anchor insertion limiting means comprising a protruding stopping member 142 disposed on the exterior surface 144 of the plunger 102 distal from the tapered end 136. The operation of the plunger 102 and the insertion member 100 as an installation tool for deploying a suture anchor are discussed hereinafter.

Figures 5, 7:
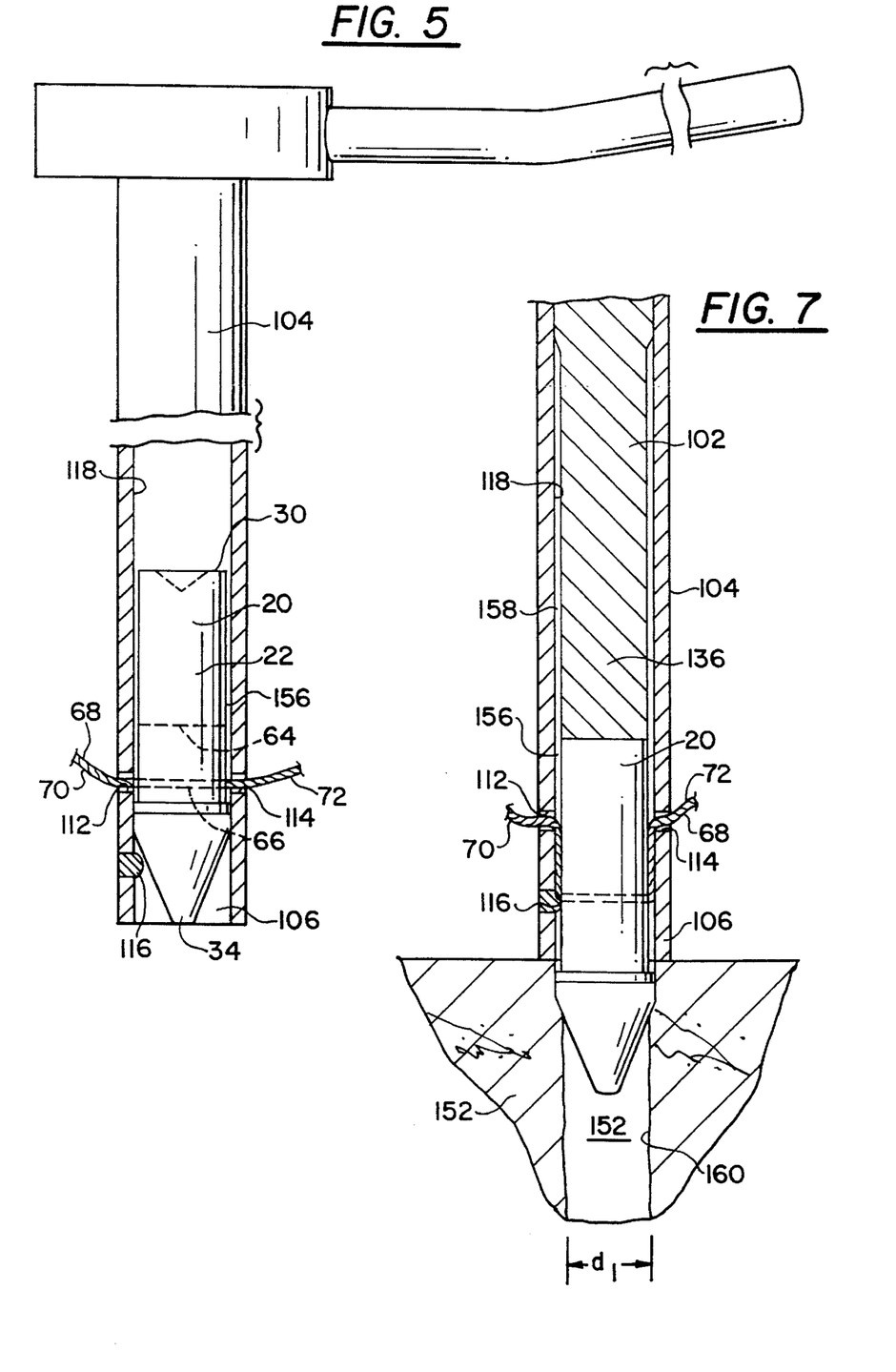
FIG. 5 is a front elevational view, partially in section, showing the suture anchor device of FIG. 1 loaded into the suture anchor insertion device shown in FIG. 4.
FIG. 7 is a front sectional view showing the insertion of the suture anchor into bone according to the present invention.

Referring now to FIG. 5, there is shown a suture anchor 20 loaded into the end 106 of the elongated body 104. The anchor 20 is loaded such that the end 30 of the body 22 first enters the elongated body 104. This is typically referred to as retrograde or muzzle loading. It is to be understood, however, that any method of loading the anchor 20 into the elongated body 104 so that the anchor 20 is positioned within the elongated body 104 as shown in FIG. 5 is sufficient for the purposes of this invention.

Loading of the suture anchor 20 is accomplished by manually pushing it into the elongated body 104. The anchor 20 is then manually rotated (if necessary) until the slot 64 aligns with the protruding appendage 116 within the elongated body 104. Thereafter the anchor 20 is pushed into the elongated body 104 such that the slot 64 aligns the holes 112 and 114.

In the loaded position, the apex 34 of the anchor 20 is flush with the end 106 of the elongated body 104 so that the anchor 20 is fully within the elongated body 104, and the outer edge portions of the base are resting proximate the interior surface 118 of the elongated body 104. A gap 156 is provided between the exterior surface of the body 22 and the interior surface 118 of the elongated body 104.

A length of suture 68 is loaded into the suture anchor 20 by inserting the suture straight through the hole 112, through the slot 64, and out through the hole 114. When the suture 68 is so loaded, a first suture end 70 extends from one side of the elongated body 104, a second suture end 72 extends from the opposite side of the elongated body 104, and an intermediate portion 66 is positioned within the slot 64. It is to be understood that the suture 68 can be of any type used in surgical procedures and can be threaded or loaded as described above with a needle (not shown) attached thereto. The suture 68 can quickly and easily be unloaded or withdrawn from the suture anchor 20 by pulling on either end 70 or 72, thus enabling one suture to be quickly replaced with another in the same anchor 20 and without removing the anchor 20 from the insertion device. Moreover, speed and ease of loading the suture 68 are facilitated by providing a straight path for the suture when loading it into the anchor 20.

Figures 6, 8:
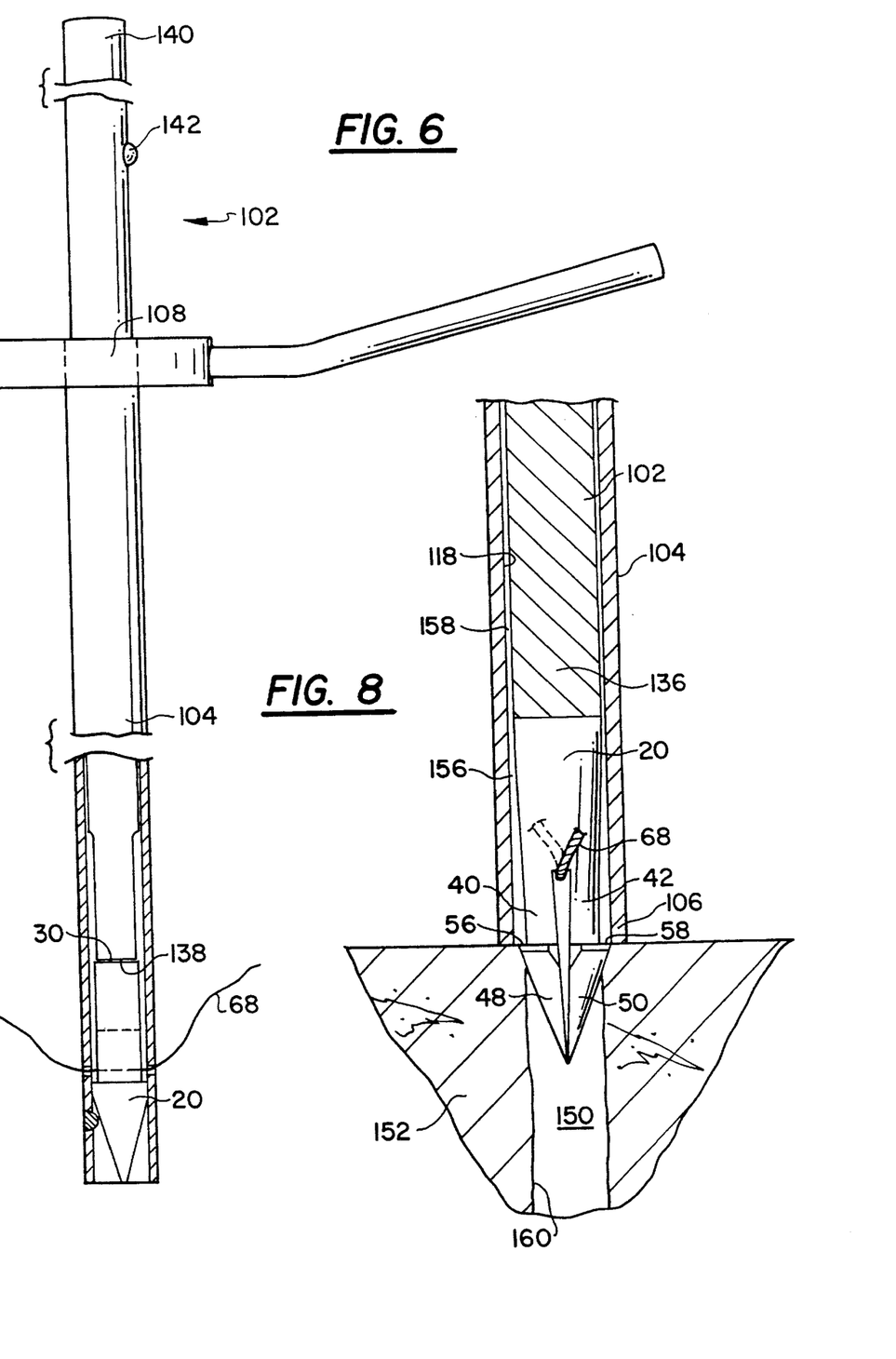
FIG. 6 is a front elevational view, partially in section, showing the suture anchor device of FIG. 1 loaded into the insertion device with the plunger positioned within the suture anchor insertion device.
FIG. 8 is a fragmented side sectional view showing the insertion of the suture anchor into bone according to the present invention.

Referring now to FIG. 6, the operation of the plunger 102 for deploying the suture anchor 20 from the elongated body 104 will be discussed. The plunger 102 is adapted to inserted into the elongated body 104 through an opening in the end 108 and slidably positioned therein such that the end surface 138 cooperates with the end 30 of the anchor 20. It is to be understood that the end surface 138 and the end 30 of the anchor 20 can be of any configuration which permits an engaging relationship therebetween. For example, the end surface 138 of may be of conical shape so to as enter the depression 64, shown in FIGS. 1–3.

The plunger 102 is slidable within the elongated body 104 so as to force the anchor 20 from the end 106 of the elongated body 104. End portion 140 of the plunger 102 extends from the upper end portion 108 of the elongated body 104 thereby providing a means for actuating the plunger 102. When the plunger 102 initially engages the anchor 20 within elongated body 104, the protruding stopping member 142 is positioned above the end portion 108 of the elongated body 104. In this position, the plunger 102 and elongated body 104 define an installation tool for inserting the suture anchor 20, including a suture 68 loaded therein, into a bore formed in a bone (not shown).

Figures 9, 10:
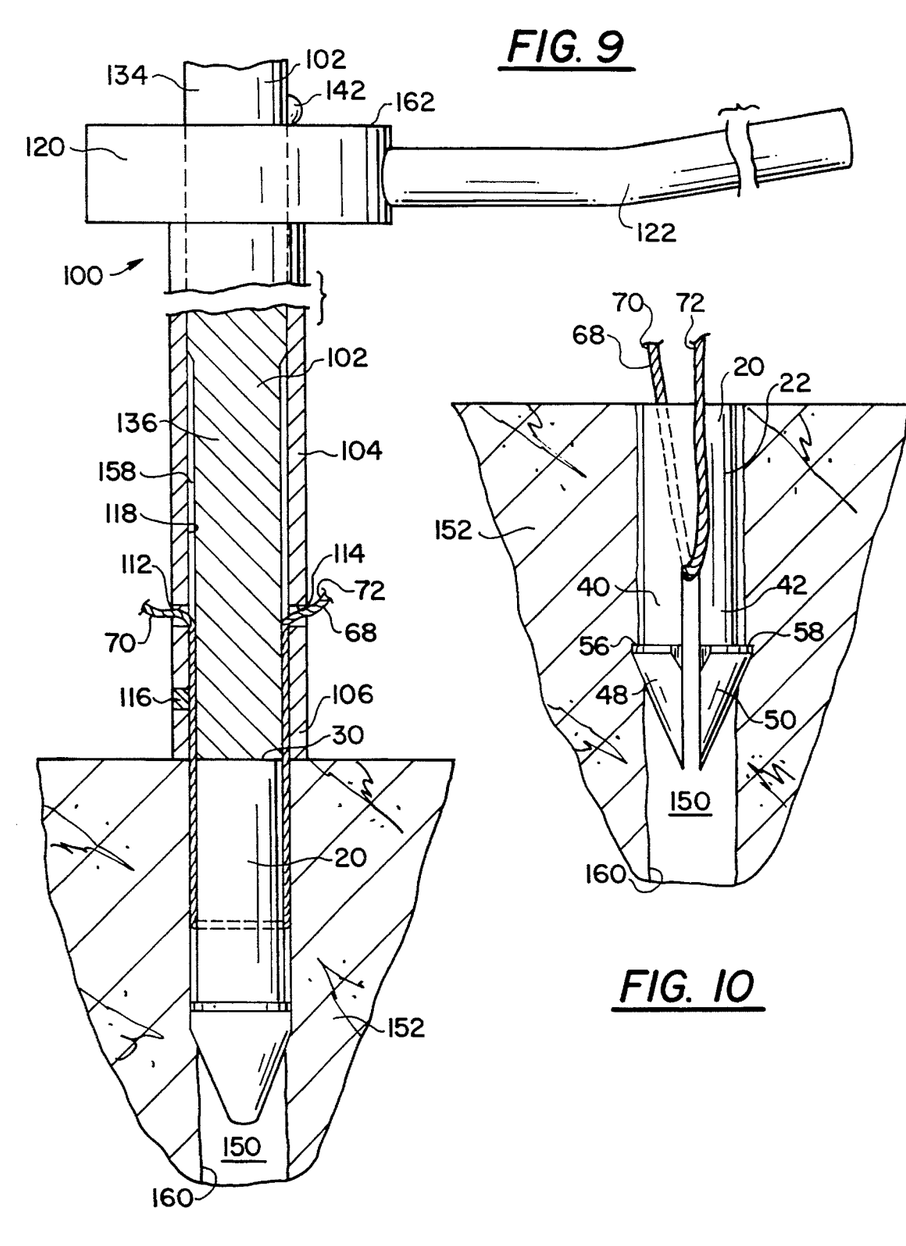
FIG. 9 is front elevational view, partially in section, showing the suture anchor being inserted into bone according to the present invention.
FIG. 10 is a side sectional view of a bone with the suture anchor as shown in FIG. 1 inserted and the installation tool removed from the insertion area.

Referring now to FIGS. 7–9, the operation of the suture anchor installation tool to insert a suture anchor 20 into a bone 152 will be discussed. A bore 150 is first formed in the bone 152 so that the suture anchor can be inserted into it. It is to be understood that the bore 150 may be formed or prepared in the bone 152 by any conventional method. In exemplary embodiment, the bore 150 is drilled to a predetermined depth and has diameter, $d_1$ (FIG. 7) preferably sized so as to be no greater than the diameter, d, of the body 22 (FIG. 1). Typically the diameter of the bore, $d_1$, is 2.5 to 4.5 mm depending on the density of the bone. The denser the bone, the greater the diameter $d_1$ is required. After the bore has been prepared, the anchor 20 has been loaded into the elongated body 104, the suture 68 has been loaded into the anchor 20, and the plunger 102 has been positioned in the elongated body 104, the suture anchor 20 is ready to be inserted into the bore 150. When moving the loaded installation tool to the insertion location, the anchor 20 is held in place in the elongated body 104 by maintaining tension on the first and second suture ends 70 and 72. The user holds the insertion member 100 in one hand by its handle 122, while the other hand maintains tension on the suture ends 70 and 72. End 106 of the elongated body 104 is then positioned over the bore 150 such that its end surface is flush with the bone 152. Downward pressure on the plunger 102, for example, a gentle tapping on its upper end portion (not shown in FIGS. 7–9), moves the suture anchor 20 toward the bore 150. The downward force of the plunger 102 then ejects the anchor 20 from the elongated body 104 thereby pulling the suture 68 through the holes 112 and 114 into the interior portion of the elongated body 104. The gap 156 provided between the suture anchor 20 and the interior surface 118 of elongated body 104 provides sufficient room for the suture to be pulled within the interior of the elongated body 104 without interfering with the sliding relationship between the suture anchor 20 and the interior of the elongated body 104. A second gap 158 is also provided between the tapered end 136 of the plunger 102 and the interior surface 118 of elongated body 104. This gap 158 enables the suture 68 to pass between the tapered end 136 of the plunger 102 and the interior surface 118 of the elongated body 104. The gap 158 is of a sufficient length to allow the suture 68 to pass between the plunger 102 and the interior surface 118 as needed to fully insert the anchor 20 into the bore 150. It can be appreciated that the slot 64 cooperates with the appendage 116 as the anchor 20 is expelled from the elongated body 104. Because the appendage 116 occupies a relatively small portion of the interior surface 118 of the elongated body 104, the suture 68 is able to slip around the appendage 116 during insertion, whereby the appendage does not interfere with the suture insertion operation.

As the suture anchor 20 enters the bore 150, the exterior surfaces of the tapered portions 48 and 50 engage the side wall 160 of the bore 150 thereby enabling tines 40 and 42 to flex toward one another. The tines 40 and 42 are made from a sufficiently resilient material such that once flexed from an undeformed position (shown in FIG. 1) to a deformed position (shown in FIG. 8), they have a tendency to return to the undeformed position, see FIG. 10. The resiliency in the tines 40 and 42 creates a spreading force urging them apart. This force secures the outer edge portions 56 and 58 against the side wall 160 of the bore 150.

As shown in FIG. 9, the suture anchor 20 is inserted into the bore 150 to a predetermined depth which is dependent upon the positioning of the protruding stopping member 142 on the body 134 of the plunger 102. The stopping member 142 is disposed on the plunger 102 such that the stopping member 142 engages a surface 162 of the flange 120 when the end 30 of the suture anchor 20 is flush with the surface of the bone 152. In this manner the anchor 20 can be repeatedly inserted to a precise depth, and because the end portion 106 of the elongated body 104 is not inserted into the bore 150, no judgment by the surgeon is needed to determine how far into the bone the anchor 20 is inserted.

Once the suture anchor 20 is inserted into the bone 152 to the predetermined depth, the insertion member 100 and plunger 102 are removed from the insertion site. As this occurs the suture 68 is held in place by the anchor 20 permitting the insertion member 100 to be pulled free of the suture ends.

In the inserted position, shown in FIG. 10, the suture anchor 20 is fully disposed within the bore 150. It is to be understood, however, that the anchor 20 may be inserted such that a portion of the body 22 remains outside the bore, so long as the bore-engaging edges 56 and 58 contact the side wall 160. Also, the anchor 20 can be inserted deeper into the bore 150 than shown in FIG. 10 if the stopping member 142 is positioned closer to the end portion 140 of the plunger 102.

As stated previously, the suture anchor 20 is prevented from being pulled out of the bore by engagement of the edges 56 and 58 with the side wall 160 of the bore 150, the edges being held against the side wall by the spreading force of the tines 40 and 42. The suture ends 70 and 72 extend from the bore 150 on either side of the body 22 providing a symmetrical load on the anchor 20. The suture ends 70 and 72 can then be used to affix tissue to the bone by any conventional tying method.

It will thus be seen that the objects of this invention have been fully and effectively accomplished. It should be appreciated, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A system for anchoring tissue to a bone, wherein the bone has a bore defined therein comprising:

a suture anchor adapted to be inserted within said bore, said suture anchor comprising:

a generally cylindrical body portion integrally and coaxially joined to a conical portion, said conical portion having a base, an exterior surface, and an apex, the conical portion being joined to one end of said body portion at said base; and a suture receiving slot formed in said anchor, said suture receiving slot extending axially along said anchor from said apex into said body portion so as to define a first flexible tine and a second flexible tine on opposite sides of said slot, said first flexible tine and said second flexible tine adapted to engage a wall of said bore, and said body portion and said first and second flexible tines being formed from a material suitable for human implantation; and a length of surgical suture positioned within said suture receiving slot such that a portion of said suture extends from said bore for securing said tissue to said bone.

2. A suture anchor as defined in claim 1, wherein base has a diameter greater than that of said cylindrical body portion thereby exposing in each tine an outer edge portion of said base.

3. A suture anchor as defined in claim 2, wherein said tines have tapered end portions corresponding to said exterior surface of said conical member, said slot enabling the tines to flex toward one another as said suture anchor is inserted into a bore formed in a bone, the tines being sufficiently resilient that upon being flexed from an undeformed position to a deformed position the tines have a tendency to return to said undeformed position so as to urge said outer edge portions of said base into engagement with a side wall of said bore.

4. A suture anchor installation tool for inserting a suture anchor of the type comprising a generally cylindrical body portion integrally and coaxially formed to a conical portion, said conical portion having a base, an exterior surface, and an apex, the conical portion being joined to one end of said body portion at said base, and at least one slot formed in said anchor for receiving the suture, said slot extending axially of the anchor from said apex into said body portion so as to define at least first and second flexible tines on opposite sides of said slot, said suture anchor installation tool comprising:

a suture anchor insertion member comprising an elongated body having a hollow interior sized so as to accommodate said suture anchor therein, a first end from which said suture anchor is expelled, and a second end, said elongated body including a suture loading assembly disposed proximate to said first end for enabling suture to be loaded within the slot formed in said suture anchor by threading said suture straight through said suture receiving slot while the anchor is fully retained within said elongated body.

5. A suture anchor installation tool as defined in claim 4, wherein said insertion member includes suture anchor aligning means for positioning said suture anchor within said elongated body such that said slot is aligned with the suture loading assembly.

6. A suture anchor installation tool as defined in claim 5, wherein said suture loading assembly comprises first and second holes through said elongated body, said holes being disposed on opposite sides of the elongated body such that when said suture anchor is positioned within said elongated body, the holes and said slot are aligned whereby a suture can be inserted straight through said first hole, through said slot, and through said second hole such that a first suture end extends from one side of said elongated body, a second suture end extends from an opposite side of said elongated body, and an intermediate portion of said suture is disposed within said suture receiving slot.

7. A suture anchor installation tool as defined in claim 5, wherein said aligning means comprises a protruding appendage disposed on an interior surface of said elongated body between said first end portion and said suture loading assembly, said protruding appendage cooperating with said suture receiving slot to align said slot with said first and second holes when said anchor is loaded into said elongated body.

8. A suture anchor installation tool as defined in claim 5, further comprising a plunger for deploying said suture anchor from said elongated body, said plunger being slidable within said elongated body and including an end portion having an end surface cooperating with an end of said body portion opposite said one end thereof for forcing said anchor from said elongated body when actuated, said plunger having a means for limiting movement of the plunger with the elongated body thereby enabling said anchor to be inserted into said bore a predetermined depth.

9. A suture anchor installation tool as defined in claim 8, wherein said predetermined depth corresponds to a distance into said bore wherein said opposite end of the body portion is flush with a surface of said bone.

10. A suture anchor installation tool as defined in claim 8, wherein said base of the conical portion of the suture anchor has a diameter greater than that of said cylindrical body portion and wherein the diameter of the end portion of the plunger substantially corresponds to that of said body portion of the suture anchor.

11. A suture anchor installation tool as defined in claim 8, wherein said means for limiting movement of the plunger comprises a protruding stopping member disposed on an exterior surface portion of said plunger remote from said tapered end portion, said protruding stopping member engaging a second end portion of said elongated body for preventing said plunger from further movement within the elongated body.

12. A suture anchor installation tool as defined in claim 5, wherein said second end portion of the elongated body includes a flange and a handle attached to the flange.

13. A suture anchor installation tool as defined in claim 12, wherein said handle comprises a rod member extending from said flange, said rod member having a first end portion attached to said flange, a second end portion, and a midsection disposed therebetween, said midsection having a bend therein.

14. A method of anchoring an intermediate portion of a suture within a bore formed in a bone for allowing tissue to be attached to said bone, comprising the steps of:

inserting a suture anchor into an installation tool, said anchor comprising:

(1) a generally cylindrical body portion integrally and coaxially joined to a conical portion having a base, an exterior surface, and an apex, the conical portion being joined to one end of said body portion at said base; and (2) at least one slot formed in said anchor for receiving the suture, said slot extending axially of the anchor from said apex into said body portion so as to define at least first and second flexible tines on opposite sides of said slot;

and said suture anchor installation tool comprising:
- a suture anchor insertion member comprising an elongated body having a hollow interior sized so as to accommodate said suture anchor therein, a first end from which said suture anchor is expelled, and a second end, said elongated body including a suture loading assembly disposed proximate to said first end;

loading a suture having first and second ends, and a intermediate portion disposed therebetween, into said slot such that said intermediate portion of the suture is positioned within the slot;

forming a bore in said bone, said bore having a diameter substantially corresponding to that of said body portion of the suture anchor;

actuating said installation tool to insert said suture anchor, having a suture threaded therein into said bore such that said intermediate portion of the suture is retained within said bore, and said first and second suture ends extend outside the bore; and affixing tissue to said bone using said first and second suture ends.

15. A method of claim 14, wherein said step of inserting said suture anchor into the installation tool comprises:

loading the suture anchor into said elongated body, such that the conical portion is last to enter the first end of said elongated body;

positioning the suture anchor within said interior of the elongated body such that said slot aligns with a pair of holes disposed on opposite sides of said elongated body;

inserting said anchor therein;

wherein the suture loading step includes passing the suture through said aligned holes and slot whereby the ends of said suture extend respectively from opposite sides of said elongated body; and the method comprising the further steps of:

inserting a plunger into said elongated body from said second end thereof such that said plunger abuts an end of said body portion of the suture anchor opposite said one end thereof;

aligning said first end of the elongated body over said bore in the bone such that first end of the elongated body is adjacent said bone surrounding said bore;

actuating said plunger to force said suture anchor and the suture seated therein from said elongated body into said bore; and moving said elongated body away from the bone such that said suture ends extend outside said bore enabling tissue to be attached to said bone using said ends of the suture.

16. The method of claim 15, wherein said step of inserting said plunger into the elongated body includes maintaining tension on the ends of said suture to hold the suture anchor in the elongated body against force applied thereon by said plunger.

17. The method of claim 15, wherein said step of actuating said plunger is accomplished by gently tapping a distal end portion of said plunger.

18. The method of claim 15, wherein said step of positioning said suture anchor within the interior of said elongated body is accomplished by manually rotating said suture anchor when it is partially within the elongated body such that said slot receives a protruding appendage disposed on the interior of the elongated body.

19. The method of claim 15, wherein said step of loading said suture into the slot in said suture anchor is accomplished by threading said suture straight through a first one of said pair of holes in said elongated body, through said slot and out a second one of said pair of holes.

\* \* \* \* \*